United States Patent [19]

Bergamaschi et al.

[11] Patent Number: 4,499,107
[45] Date of Patent: Feb. 12, 1985

[54] METHOD FOR TREATING INFECTED RENAL CALCULOSIS

[75] Inventors: Mario Bergamaschi, Monza; Carlo Alfieri, Milan, both of Italy

[73] Assignee: Dr. L⁰. Zambeletti, S.p.A., Milan, Italy

[21] Appl. No.: 435,291

[22] Filed: Oct. 19, 1982

[30] Foreign Application Priority Data

Nov. 5, 1981 [IT] Italy .............................. 24897 A/81

[51] Int. Cl.³ ........................................... A61K 31/165
[52] U.S. Cl. .................................................. 514/575
[58] Field of Search ........................................ 424/324

[56] References Cited

PUBLICATIONS

Chem. Abst., 10th Coll. Index Ring Systems–Formulas, A–$C_6H_4T_2$–723F.
Chem. Abst., 94–10876v (1980).

Primary Examiner—Stanley J. Friedman
Attorney, Agent, or Firm—Walter H. Schneider

[57] ABSTRACT

Pharmaceutical compositions suitable for the therapy of infected renal calculosis, containing propionhydroxamic acid as an active principle, are described.

3 Claims, No Drawings

METHOD FOR TREATING INFECTED RENAL CALCULOSIS

The present invention relates to a new pharmaceutical composition for the therapy of infected renal calculosis, characterized in that it comprises, as active principle, propionhydroxamic acid having formula (I)

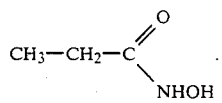
(I)

The use of acetohydroxamic acid (AHA), $CH_3CONHOH$, for the therapy of infected renal calculosis, is already known. For instance, A. Martelli et al. (Urology, vol. XVII, 4, p.320 and followings (1981)) has pointed out the efficacy of such a compound in the treatment of renal lithiasis sustained by urease-producing bacteria, evidencing that the drug's action is devoted to decrease of urinary ammonium and urinary pH, and to enhancement of antibiotic therapy.

However, it is also known that AHA shows teratogenic effects. S. Caube et al. (Cancer Res. 26, 1448 (1966)) observed that i.p. administration of 750 mg/kg una tantum of acetohydroxamic acid to pregnant female rats, on the 12$^{th}$ day of pregnancy, causes deformations in 50% of fetuses; a dose of 1000 mg/kg, in the same conditions, causes deaths in 55% of fetuses, and deformations in 100% of the survived fetuses; finally, a dose of 1500 mg/kg causes 100% reabsorption of fetuses. Also Th. Von Kreybig et al. (Arzneimittel-Forschung 18, 645-657 (1968)) pointed out the teratogenic activity of AHA, substantially confirming the results of Caube.

Another negative aspect of the therapy with AHA is the mutagenic action of this compound.

E. Borenfreund et al. (J. Nat. Cancer Inst. 32, 667 (1964)) showed that the addition of AHA at a $1,1.10^{-4}M$ concentration to mouse and chinese hamster embryonal cell cultures causes morphological changes of the chromosomes provoked by damages at DNA.

In the Belgian Pat. No. 878,836, Jan. 16, 1980, it is moreover reported that AHA is mutagenic according to the Ames test on two strains of *Salmonella typhimurium* (TA 100 and TA 98), at the dose of 40,000 μg/plate.

These negative aspects of AHA are unfortunate since the therapy of infected renal calculosis with such a compound leads to undeniably appreciable results.

It has now been found that for the same therapy it is possible to use advantageously the propionhydroxamic acid (I) (which will be hereinafter designated with the abbreviation PHA), which on the contrary appears devoid of mutagenic and teratogenic effect.

The systematic comparison between acetohydroxamic acid and propionhydroxamic acid led to the following results.

Behavioral study according to Irwin. The two substances, administered by oral route at the dose of 1000 mg/kg, evidence a qualitatively and quantitatively similar phenomenology: same reduction of the vigilance, decrease of the motor activity, slight ptosis and slight bradhypnea, of the same intensity for the two substances. For both substances, the asymptomatic dose is less than 250 mg/kg.

Cardiovascular tolerance. In the rabbit the two products, administered by oral route at the dose of 100 mg/kg, induce a slight reduction (20%) of the arterial pressure which is short lasting for PHA (10-30 min.) and long lasting for AHA (>120 min.).

At this dose, the heart rate is not modified by both drugs. At the dose of 50 mg/kg per os PHA does not change either the blood pressure or the heart rate while AHA causes a 15% reduction of the mean arterial pressure, which is still present 120 minutes after the administration.

Acute toxicity. The acetohydroxamic acid and the propionhydroxamic acid administered by oral route in the mouse have a very close acute toxicity: in fact the calculated $LD_{50}$'s are 2741 (confidence limits 2052-2971) mg/kg for AHA and 2366 (confidence limits 1726-3243) mg/kg for PHA. (The data obtained by T. von Kreybig et al. (Arzneim. Forsch. 18, 645 (1968)) are partially in contrast with ours: it is deemed that von Kreybig had used products of less purity grade.

Subacute toxicity. A test lasting 4 weeks has been carried out on the two compounds administered at the dose of 200 mg/kg by oral route to groups of "Wistar" rats, 8 males and 8 females, with daily observation of the behavior, of health status, of feed and water consumption and, twice a week, of the body weight of animals. At the end of 4 weeks the animals have been sacrificed and autopsy and haematological and haematochemical examinations have been performed on them. For all the duration of the test, no anomaly has been noticed in the behavior of both AHA-treated and PHA-treated animals.

Already after the first days of treatment with AHA, a decrease of feed consumption and of weight increase was noticed in rats of both sexes in comparison with control groups.

Also in the rats treated with PHA, a decrease of feed consumption and of body weight increase was noticed, which was slightly more marked than that noticed in the animals treated with AHA.

The autoptical examination of the both AHA-treated and PHA-treated animals allowed to observe hypotrophy of the main organs (thymus, testes, heart, liver) which nevertheless showed no macroscopic lesion. No remarkable differences were observed in haematochemical parameters between AHA and PHA.

Mutagenesis. As far as AHA is concerned, it has been previously reported. The same trial, carried out with PHA at $1.1\ 10^{-4}M$ concentration on mouse and chinese hamster embryonal cell cultures, did not induce, after 24-72 hours of incubation, any morphologic change of the chromosomes, provoked by damages at DNA. The propionhydroxamic acid is non mutagenic also in the Ames test.

Theratogenesis. The theratogenic activity of AHA has been already shown.

The propionhydroxamic acid, administered by intraperitoneal route, only once on the 13$^{th}$ day of pregnancy in female rats, at the dose of 300 mg/kg, increases the number of dead fetuses in comparison with AHA (55% against 50%), but the survived fetuses show a perfectly normal development from the morphological point of view.

The results shown above, pointing out a globally superimposable behavior of AHA and PHA, with the exclusion of the fundamental aspects of the mutagenesis and of the theratogenesis, which are absent in propionhydroxamic acid, prompted to test this latter compound on some clinical cases, hereunder reported.

CASE NO. 1 (G.S., 32 YEARS OLD, MALE)

(1) Urinary infection caused by urease-producing bacteria;
(2) relapsing renal calculosis.

Right nephrolithotomy because of multirelapsing staghorn renal calculosis. After the operation, a *Proteus mirabilis* urinary infection being present, courses of specific antibiotic therapy have been performed for two months, with negative results.

The combination of propionhydroxamic acid at the dose of 500 mg/die with the antibiotic therapy led to sterilization of urinary cultures and to normalization of pH and urinary ammonium values.

After 5 months' therapy, neither side effects due to the drug, nor presence of lithiasic relapse were noticed.

CASE NO. 2 (O.L., 57 YEARS OLD, MALE)

(1) Urinary infection caused by urease-producing bacteria;
(2) relapsing renal calculosis.

Nephrectomized at the left side because of multirelapsing staghorn lithiasis. Right lower polar nephrectomy with removal of a staghorn calculus.

Lithiasic relapse at the right side. The patient has constantly shown an urinary infection supported by both *Proteus mirabilis* and Klebsiella with marked alkalinity of the urine and urinary ammonium level higher than 150 mM/L.

The antibiotic therapy performed according to the antibiograms of urinary cultures was not successful on the urinary infection. The combination of propionhydroxamic acid, at the dose of 375 mg/die, and antibiotic therapy, led to a sufficient urinary acidification, to a decrease of urinary ammonium values and to a resolution of urinary infection. The temporary interruption of the drug caused a reapparence of urease producing bacteria (Klebsiella). Side effects as well as volumetric increase of the lithiasic relapse were not observed during 5 months' therapy.

CASE NO. 3 (V.O., 35 YEARS OLD, FEMALE)

(1) Urinary infection caused by urease-producing bacteria;
(2) relapsing renal calculosis.

Two operations of nephrolithotomy at the right side and one of bivalvular nephrolithotomy at the left side. She has now right renal staghorn calculosis in seriously pyelonephritic right kidney.

The chemical composition of the removed stones proved to be ammonium-magnesium phosphate and carbonate-apatite. The patient yet shows a *Proteus mirabilis* urinary infection with bacterial count $10^5$ b/ml, in spite of the courses of antibiotic therapy performed during the last 8 months. The combination of propionhydroxamic acid at the dose of 500 mg/kg allowed a normalization of the urinary ammonium with finding of non pathologic crystalluria. Side effects due to the drug administration were absent. Absence of lithiasic relapse at the left kidney.

CASE NO. 4 (D.S., 37 YEARS OLD, FEMALE)

(1) Urinary infection caused by urease-producing bacteria;
(2) relapsing renal calculosis.

Right nephrolithotomy surgery in 1976 and 1978; left nephrolithotomy in 1980. She now shows right renal staghorn calculosis. A new right nephrolithotomy has been planned. The chemical composition of the removed stones proved to be ammonium-magnesium phosphate and calcium carbonate. The patient had in the past and yet has a urinary infection sustained by *Proteus mirabilis* and Klebsiella. The combination of propionhydroxamic acid at the dose of 500 mg/die with the antibiotic therapy led, after 3 months of administration, to a normalization of ammonium values, urinary pH and crystalluria which are found constantly pathological in previous checks. No side effects as well as no lithiasic relapse at the left kidney were observed.

CASE NO. 5 (M.G., 30 YEARS OLD, MALE)

(1) Urinary infection caused by urease-producing bacteria;
(2) relapsing renal lithiasis.

Nephrectomized at the right side because of a relapsing staghorn renal calculosis. Undergone to operation of left bivalvular nephrotomy for the removal of a staghorn calculus of the pelvis and of calyces.

The chemical compositions of the removed stone proved to be ammonium magnesium phosphate and calcium carbonate. The patient, after the operation, continued to show a persistent urinary infection by *Proteus mirabilis* with high values of urinary ammonium (150 mM/L), and marked alkalinity of urinary pH and remarkable struvite and carbonate-apatite crystalluria.

After 8 months from the operation of left nephrolithotomy the patient had a lithiasic relapse localized at the upper calyx. The numerous and continuous courses of antibiotic therapy that the patient carried out during 4 years neither corrected the urinary infection, nor normalized the chemico-physical urinary parameters.

The combination with the antibiotic therapy of priopionhydroxamic acid led to a normalization of urinary ammonium and pH, to a resolution of urinary infection, to a stopping of the growth of the already present lithiasic formation and to a lacking onset of further relapses.

The used dosage has been 500 mg/die; side effects were not observed during the first 3 months' therapy.

The present invention relates to all the applicable industrial aspects connected with the use of propionhydroxamic acid as agent suitable to normalize ammonium and urinary pH, to resolve the urinary infection, to stop the growth of lithiasic formations and to avoid the onset of relapses. Therefore, an essential aspect of the invention is represented by pharmaceutical compositions containing predetermined amounts of PHA or of its pharmaceutically acceptable salts choosen among the inorganic salts such as, for example: Sodium, Potassium, Calcium, Magnesium etc. or organic salts such as, for instance: glucosamine, tromethamine, aminoacids such as, for instance, Lysine, Arginine, etc. PHA can be administered (by oral route) both as free acid and as its pharmaceutically acceptable salts in form of capsules in mixture with suitable inert excipients or in form of tablets or sugar-coated pills, dispersable powder and the like, containing besides PHA and its salts the above cited inert diluents and/or dispersing agent, colouring and flavouring agents etc.

These formulations can be administered once or more times a day, and they can contain from about 25 to about 500 mg, preferably from 50 to 250 mg, of PHA or equivalent amounts of the previously cited salts.

Non-limitative examples are the following:
capsules, containing 72.5–125–250 mg of PHA; expressed as free acid;

tablets, containing 72.5–125–250 mg of PHA; expressed as free acid;

sugar-coated pills, containing 72.5–225–250 mg of PHA; expressed as free acid.

We claim:

1. A method of treating infected renal calculosis which comprises orally administering to a patient a composition containing as the active ingredient from about 25 mg to about 500 mg of proprionic hydroxamic acid expressed as free acid, or an equivalent amount of a pharmaceutically acceptable salt thereof, in admixture with a pharmaceutically acceptable carrier.

2. A method according to claim 1 in which the salt is selected from sodium, potassium, calcium, magnesium, glucosamine, tromethamine, lysine and arginine.

3. A method according to claim 2 containing as the active ingredient from about 50 mg to about 250 mg of proprionic acid expressed as the free acid, or an equivalent amount of a salt.

* * * * *